(12) United States Patent
Augustine

(10) Patent No.: US 8,168,562 B2
(45) Date of Patent: May 1, 2012

(54) PREPARATION OF PALLADIUM-GOLD CATALYSTS

(75) Inventor: Steven M. Augustine, Ellicott City, MD (US)

(73) Assignee: Lyondell Chemical Technology, L.P., Houston, TX (US)

(*) Notice: Subject to any disclaimer, the term of this patent is extended or adjusted under 35 U.S.C. 154(b) by 1312 days.

(21) Appl. No.: 11/346,500

(22) Filed: Feb. 2, 2006

(65) Prior Publication Data

US 2007/0179310 A1 Aug. 2, 2007

(51) Int. Cl.
| | |
|---|---|
| *B01J 27/02* | (2006.01) |
| *B01J 27/055* | (2006.01) |
| *B01J 27/043* | (2006.01) |
| *B01J 27/045* | (2006.01) |
| *B01J 23/58* | (2006.01) |
| *B01J 23/42* | (2006.01) |
| *B01J 23/00* | (2006.01) |
| *C01G 23/047* | (2006.01) |
| *C07C 67/00* | (2006.01) |

(52) U.S. Cl. ........ 502/334; 502/216; 502/218; 502/222; 502/223; 502/330; 502/350; 423/610; 560/241

(58) Field of Classification Search .......... 502/216, 502/218, 222, 223, 330, 334, 350; 423/610
See application file for complete search history.

(56) References Cited

U.S. PATENT DOCUMENTS

| | | | | |
|---|---|---|---|---|
| 3,743,607 | A | | 7/1973 | Sennewald et al. ........... 252/430 |
| 3,775,342 | A | * | 11/1973 | Kronig et al. ................. 502/170 |
| 3,925,452 | A | * | 12/1975 | Swodenk et al. ............. 560/245 |
| 3,970,697 | A | | 7/1976 | Scheben et al. ............... 260/533 |
| 4,139,491 | A | * | 2/1979 | Dorawala et al. ............. 502/439 |
| 4,188,490 | A | | 2/1980 | Hinnenkamp et al. |
| 5,017,699 | A | | 5/1991 | Suen ............................. 544/196 |
| 5,250,487 | A | | 10/1993 | Wirtz et al. ................... 502/243 |
| 5,338,715 | A | | 8/1994 | Iida et al. ........................ 502/64 |
| 5,591,414 | A | | 1/1997 | Jacob et al. .................... 422/180 |
| 5,679,313 | A | | 10/1997 | Nojima et al. ................. 423/237 |
| 5,710,084 | A | | 1/1998 | Nojima et al. ................... 502/66 |
| 5,728,356 | A | | 3/1998 | Iida et al. .................... 423/239.1 |
| 5,911,961 | A | | 6/1999 | Horiuchi et al. ........... 423/213.5 |
| 6,022,823 | A | | 2/2000 | Augustine et al. ............ 502/243 |
| 6,180,556 | B1 | | 1/2001 | Marella et al. ................ 502/217 |
| 6,498,259 | B1 | | 12/2002 | Grey et al. ..................... 549/533 |
| 6,849,243 | B1 | | 2/2005 | Hagemeyer et al. .......... 423/344 |
| 6,855,661 | B2 | | 2/2005 | Kim .............................. 502/219 |
| 7,067,092 | B2 | | 6/2006 | Hall et al. |

FOREIGN PATENT DOCUMENTS

| | | |
|---|---|---|
| JP | 06-071181 | 3/1994 |
| WO | WO 2005/061107 | 7/2005 |
| WO | WO 2007/094903 A2 | 8/2007 |
| WO | WO 2007/094903 A3 | 10/2007 |

OTHER PUBLICATIONS

Shanmugam Yuvaraj, Lin Fan-Yuan, Chang Tsong-Huei, and Yeh Chuin-Tih, Thermal Decomposition of Metal Nitrates in Air and Hydrogen Environments, *J. Phys. Chem. B 2003*, 107, 1044-1047.

* cited by examiner

*Primary Examiner* — Patricia L Hailey

(57) ABSTRACT

A new method for preparing supported palladium-gold catalysts is disclosed. The method comprises sulfating a titanium dioxide support, calcining the sulfated support, impregnating the calcined support with a palladium salt, a gold salt, and an alkali metal or ammonium compound, calcining the impregnated support, and reducing the calcined support. The resultant supported palladium-gold catalysts have increased activity and stability in the acetoxylation.

16 Claims, No Drawings

PREPARATION OF PALLADIUM-GOLD CATALYSTS

FIELD OF THE INVENTION

The invention relates to supported palladium-gold catalysts. More particularly, the invention relates to supported palladium-gold catalysts that have increased catalytic activity and activity stability in acetoxylation.

BACKGROUND OF THE INVENTION

Palladium-gold catalysts are known. They are used in acetoxylation. For instance, the oxidation of ethylene in the presence of a palladium-gold catalyst and acetic acid produces vinyl acetate, which is a useful monomer for the polymer industry.

Acetoxylation is commonly performed by the vapor phase reaction using supported palladium-gold catalyst. Methods for supporting palladium-gold catalysts are known. In general, the method involves depositing a mixture of palladium and gold salts onto a support and then reducing the palladium and gold to metals.

Palladium and gold are both precious metals. Therefore, many efforts have been made to increase the catalytic activity and reduce the amount of catalyst needed. For example, U.S. Pat. No. 6,022,823 teaches calcining the support impregnated with palladium and gold salts prior to reducing the metals. The catalyst shows improved activity.

One challenge still facing the industry is that the supported palladium-gold catalysts are often deactivated in acetoxylation. Thus, it is important to the industry to increase the activity stability of the supported palladium-gold catalysts. Ideally, the catalyst would have increased activity or productivity but would not incur increased cost.

SUMMARY OF THE INVENTION

The invention is a method for preparing a supported palladium-gold catalyst. The method comprises sulfating a titanium dioxide support. The sulfated support is calcined. The calcined support is then treated with a solution containing a palladium salt, a gold salt, and an alkali metal or ammonium compound. The alkali metal or ammonium compound reacts with the palladium and gold salts during impregnation of the support. The impregnated support is calcined to cause partial decomposition of the palladium and gold salts. The calcined product undergoes reduction to reduce palladium and gold to metals.

The invention includes the palladium-gold catalyst prepared according to the method of the invention. The invention also includes the use of the catalyst in acetoxylation for preparing vinyl acetate and allyl acetate. Compared to the palladium-gold catalysts known in the art, the catalysts prepared according to the method of the invention show improved catalytic activity stability in acetoxylation.

DETAILED DESCRIPTION OF THE INVENTION

The method of the invention comprises sulfating a titanium dioxide support. By "sulfating," I mean introducing sulfate into titanium dioxide support. Sulfating can be done either in the titanium dioxide production process or by post treatment after the titanium dioxide is made. In the sulfate titanium dioxide process, one may control the amount of sulfate residue. Alternatively, the sulfating step can be done by treating a titanium dioxide with a sulfating agent. The sulfate-containing titanium dioxide from a sulfate titanium dioxide process or any other sources may, or may not, be further sulfated.

Suitable sulfating agents include sulfuric acid, persulfuric acid, and their salts, the like, and mixtures thereof. Preferably, the sulfating agent is a salt of sulfuric acid or persulfuric acid. The salts are more convenient to handle than the acid because they are less hazardous.

Preferably, the above sulfated titanium dioxide contains greater than or equal to 0.01 wt % of sulfur (S). More preferably, the sulfated titanium dioxide contains from 0.01 wt % to about 5 wt % of S. Most preferably, the sulfated titanium dioxide contains from 0.1 wt % to about 1.0 wt % of S.

Preferably, the titanium dioxide for use in the post treatment is produced by hydrolysis of titanium oxychloride or titanyl sulfate, is nano-structured and is crystalline anatase.

The sulfated titanium dioxide is then calcined. The calcination is performed by heating the titanium dioxide at a temperature preferably within the range of 500° C. to 900° C., more preferably 600° C. to 800° C., and most preferably 650° C. to 750° C.

Preferably, the calcined titanium dioxide has pore volumes within the range of 0.1 cm$^3$/g to 0.75 cm$^3$/g and surface areas within the range of 0.5 m$^2$/g to 500 m$^2$/g. More preferably, the pore volumes are within the range of 0.10 cm$^3$/g to 0.65 cm$^3$/g; the surface areas are within the range of 1 m$^2$/g to 200 m$^2$/g. Most preferably, the surface area is from 2 m$^2$/g to 50 m$^2$/g.

I surprisingly found that calcining the sulfated support significantly increases the acetoxylation activity of the palladium-gold catalyst prepared therefrom. One possible effect of calcining the sulfated titanium dioxide support is sintering and modifying the support surface and thus makes it a better fit for the palladium and gold metals that are supported thereupon.

The calcined support is impregnated. Any suitable impregnation methods can be used. For instance, U.S. Pat. No. 6,022,823, the teachings of which are incorporated herein by reference, teaches how to impregnate the support.

The support can be simultaneously or successively treated with a palladium salt, a gold salt, and an alkali metal or ammonium compound. Preferably, the impregnation is performed in aqueous solutions. The concentration of the solutions and the amount of each solution used is governed by the concentration of palladium and gold desired in the final catalyst product.

Suitable palladium salts include palladium chloride, sodium chloropalladite, palladium nitrate, palladium sulfate, the like, and mixtures thereof. Suitable gold salts include auric chloride, tetrachloroauric acid, sodium tetrachloroaurate, the like, and mixtures thereof. Sodium tetrachloroaurate and palladium chloride or sodium chloropalladite are most commonly used.

Suitable alkali metal or ammonium compounds include alkali metal or ammonium hydroxides, alkali metal or ammonium carbonates, alkali metal or ammonium bicarbonates, alkali metal or ammonium metasilicates, the like, and mixtures thereof.

One method to impregnate the support involves first treating the support with an aqueous solution of an alkali metal or ammonium compound. The support which has been treated with the aqueous solution containing the alkali metal or ammonium compound is then contacted with an aqueous solution containing palladium and gold salts.

In another method, the impregnation with the palladium and gold solutions is carried out before treatment with the aqueous solution of the alkali metal or ammonium compound. In this procedure the absorptive capacity of the support is essentially completely filled with the aqueous solution of palladium and gold salts. Typically, this is accomplished by dropping the solution onto the support until incipient wetness is achieved. The support impregnated with the palladium and gold salts is then contacted with the alkali metal or ammonium compound.

A third method involves mixing the alkali or ammonium compound and precious metal compounds prior to contacting with the support. The contact with the support can be done by dropping or spraying the mixture onto the support until incipient wetness or by making a slurry of a powdered support in the solution.

The impregnated catalyst is preferably washed with water to remove alkali metal salts such as chlorides formed during the impregnation and dried prior to calcination.

The impregnated support is calcined, i.e., heated at an elevated temperature in a non-reducing atmosphere. Preferably, the calcination is performed under such a condition that a portion of the palladium and gold salts are decomposed. More preferably, at least 10% of the palladium and gold salts are decomposed during the calcination.

Preferably, the calcination of the impregnated support is carried out at a temperature within the range of about 100° C. to about 600° C. More preferably, the temperature is within the range of 100° C. to 300° C. Most preferably, the temperature is within the range of 150° C. to 250° C.

Suitable non-reducing gases used for the calcination include inert or oxidizing gases such as helium, nitrogen, argon, neon, nitrogen oxides, oxygen, air, carbon dioxide, the like, and mixtures thereof. Preferably, the calcination is carried out in an atmosphere of nitrogen, oxygen or air or mixtures thereof.

The degree of decomposition of the palladium and gold salts depends on the temperature used, the deposited salt, and the length of time the deposited sulfate-containing titanium dioxide is calcined and can be followed by monitoring volatile decomposition products. For example, when the support is impregnated with palladium and gold carbonates, the amount of carbon dioxide ($CO_2$) evolved can be measured.

Following the calcination step, the resulting product is reduced to convert the palladium and gold salts to the corresponding metals. The reduction is performed by heating in the presence of a reducing agent. Suitable reducing agents include ammonia, carbon monoxide, hydrogen, hydrocarbons, olefins, aldehydes, alcohols, hydrazine, primary amines, carboxylic acids, carboxylic acid salts, carboxylic acid esters, the like, and mixtures thereof. Hydrogen, ethylene, propylene, alkaline hydrazine and alkaline formaldehyde are preferred reducing agents and ethylene and hydrogen are particularly preferred.

Temperatures employed for the reduction can range from ambient up to about 600° C. Preferably, the reduction temperature is within the range of 300° C. to 600° C. Most preferably, the reduction temperature is within the range of 450° C. to 550° C. The reduction results in a supported palladium-gold catalyst.

The invention includes the supported palladium-gold catalyst made according to the method of the invention. Preferably, the supported palladium-gold catalyst comprises 0.1 wt % to 3 wt % of palladium and 0.1 wt % to 3 wt % of gold, and the weight ratio of palladium to gold is within the range of 5/1 to 1/3. More preferably, the supported palladium-gold catalyst comprises 0.5 wt % to 1.5 wt % of palladium and 0.25 wt % to 0.75 wt % of gold; the weight ratio of palladium to gold is within the range of 2.5/1 to 1/1.5.

The supported palladium-gold catalysts made according to the invention have many uses. It can be used, for example, in the partial oxidation, hydrogenation, carbonylation, ammonia synthesis, selective hydrogenation, acetyloxylation, catalytic combustion or complete oxidation, three way catalysis, NOx removal, methanol synthesis, hydrogen peroxide synthesis, hydroformylation, alkylation and alkyl transfer, oxidative carbonylation, coupling of olefins with aromatics, and the preparation of methyl isobutyl ketone from acetone.

The supported palladium-gold catalysts made according to the invention are particularly useful for the productions of vinyl acetate and allyl acetate. Various processes for the productions of vinyl acetate and allyl acetate are known. For instance, U.S. Pat. Nos. 3,743,607 and 3,775,342, the teachings of which are herein incorporated by reference, teach how to prepare vinyl acetate using palladium-gold catalysts.

For the use in the productions of vinyl acetate and allyl acetate, the supported palladium-gold catalyst is preferably treated with a potassium compound such as potassium acetate. The potassium treatment can be done by mixing the catalyst with a potassium acetate solution, filtering, and drying the treated catalyst.

In general, vinyl acetate can be made by the oxidation of ethylene in the presence of acetic acid and the supported palladium-gold catalyst. Allyl acetate can be made by a similar manner but using propylene rather than ethylene.

I surprisingly found that the catalysts made according to the invention give not only high catalytic activity but also high activity stability. One problem in the existing palladium-gold catalysts is that the catalysts lose activity with time. This invention provides a solution to the problem.

The following examples merely illustrate the invention. Those skilled in the art will recognize many variations that are within the spirit of the invention and scope of the claims.

Example 1

Sulfating Titanium Dioxide

A titanium dioxide (20 grams, GP350 from Millennium Chemicals, prepared from hydrolysis of an aqueous solution of titanium oxychloride) is mixed with 50 ml of a 0.05 mole/l aqueous solution of ammonium persulfate at room temperature with stirring for at least two hours. The slurry is filtered, and the solid is dried for at least 16 hours in an oven at a temperature of 105° C. to yield a sulfated titanium dioxide.

Calcining Sulfated Titanium Dioxide

The sulfated titanium dioxide is calcined at 700° C. for six hours. It has a final surface area of 32.5 $m^2/g$, a pore volume of 0.20 ml/g, and a sulfur content of 0.23 wt %. The sulfur content is measured according to the following method.

A titanium dioxide sample (0.5 gram) is mixed with hydrofluoric acid (5 ml) in a sealable microwavable vessel. The mixture is heated under pressure in the microwave until in solution. After cooling, it is diluted to 50 ml with deionized water. Measurements are done using an IRIS Intrepid II inductively coupled plasma emission spectrometer and reported as percent sulfur.

Impregnation $NaAuCl_4$ (0.194 gram), $Na_2PdCl_4$ (0.496 gram), and $NaHCO_3$ (0.510 grams) are dissolved in water (20 ml). The solution is mixed with the above calcined titanium dioxide (10 grams) to form a slurry. The slurry is kept overnight to allow the metal compounds to deposit onto the surface of titanium dioxide. The mixture is filtered. The solid is washed by mixing with water (20 ml) and filtering again. It is then dried in an oven at 105° C. for at least 16 hours.

Calcining Impregnated Support

The above impregnated titanium dioxide is calcined in a reactor at 200° C. in flowing air for three hours to affect a partial decomposition in excess of 10% of the deposited precious metal salts.

Reduction

After the above calcination, the reactor is purged with nitrogen, and then a mixture of 5% hydrogen in nitrogen is introduced into the vessel. The temperature is ramped to 500° C. at a rate of 10° C./min. The temperature is held at this reading for three hours. The reactor is purged with nitrogen and the resultant catalyst is then cooled to room temperature in flowing nitrogen. Upon cooling, the sample is washed to remove any remaining chloride as determined by testing with a silver nitrate solution, and then dried at 105° C. in an oven.

Potassium Treatment

The above resultant catalyst (5 grams) is contacted with an excess (>10 ml) of 5 w % aqueous solution of potassium acetate at room temperature for 10 minutes. The mixture is filtered; the potassium treated catalyst is dried at 105° C. in an oven for at least 4 hours.

Vinyl Acetate Preparation

The potassium treated catalyst is mixed with, in a ratio of 1 to 9, an inert alumina support to minimize effects of thermal gradients. The mixture (0.5 gram) is placed in a quartz glass reactor. The temperature is raised to 110° C. and then the material is exposed to a gas feed composition of 77% ethylene, 11% helium, 9% oxygen and 3% acetic acid at atmospheric pressure and a gas-hourly space velocity of 13,200. The reactor effluent is analyzed using a mass spectrometer. The temperature is then ramped from 110° C. to 160° C. and cooled again to 110° C. repeatedly at a rate of 2° C./min.

The performance of the catalyst is compared by calculating the rate as interpolated at 135° C. at specified times on stream and is calculated from the data taken between 110° C. and 160° C. Calibrations are made by injecting known amounts of vinyl acetate. The results are listed in Table 1, which show that the catalyst exhibits high activity. Table 1 also lists the catalyst activities measured at the $1^{st}$ hour and the $6^{th}$ hour on stream. The results show that the catalyst activity increases with increased exposure to reaction conditions.

TABLE 1

Catalyst Activity and Activity Stability in Vinyl Acetate Production

| Ex. No. | Titanium Dioxide Support | S % before Impregnation | Activity at the $1^{st}$ Hour (umol/s) | Activity at the $6^{th}$ Hour (umol/s) |
|---|---|---|---|---|
| 1 | Post sulfated GP350 | 0.23 wt % | $4.23 \times 10^{-3}$ | $4.63 \times 10^{-3}$ |
| C2 | Non-sulfated GP350 | 0 | $3.40 \times 10^{-3}$ | $2.96 \times 10^{-3}$ |
| 3 | Sulfated DT51 | 0.14 wt % | $3.02 \times 10^{-3}$ | $3.39 \times 10^{-3}$ |
| 4 | Post sulfated DT51 | 0.14 wt % | $3.67 \times 10^{-3}$ | $4.42 \times 10^{-3}$ |

Comparative Example 2

The general procedure of Example 1 is repeated with the exception that the GP350 titanium oxide is not treated with ammonium persulfate. As shown in Table 1, the catalyst activity is significantly lower than that of Example 1, and the activity declines from the $1^{st}$ hour to the $6^{th}$ hour.

Example 3

The general procedure of Example 1 is repeated with the exceptions that the titanium dioxide (DT51, from Millennium Chemicals) is made using sulfate precursors and that the titanium dioxide is not treated with ammonium persulfate. The titanium dioxide contains 0.47 wt % of sulfur. After the titanium dioxide is calcined at 700° C., its sulfur content reduces to 0.14 wt %. As shown in Table 1, the catalyst shows improved activity stability compared to the catalyst of Comparative Example 2.

Example 4

The general procedure of Example 3 is repeated with the exception that the titanium dioxide is treated with 0.05 molar ammonium persulfate. As shown in Table 1, the catalyst shows improved activity compared to the catalyst of Example 3 and improved activity stability compared with the catalyst of Comparative Example 2.

TABLE 2

Effect of Calcination Temperatures on Catalyst Activity

| Ex. No. | Support Calcination Temperature | Impregnated Support Calcination Temperature | Catalyst Activity at $6^{th}$ Hour (umol/s) |
|---|---|---|---|
| 5a | Not calcined | — | $1.53 \times 10^{-3}$ |
| 5b | 700° C. | 190° C. | $3.27 \times 10^{-3}$ |
| 5c | 800° C. | 190° C. | $3.30 \times 10^{-3}$ |
| 5d | 900° C. | 190° C. | $3.57 \times 10^{-3}$ |
| 5e | 700° C. | 220° C. | $3.76 \times 10^{-3}$ |
| 5f | 800° C. | 220° C. | $3.24 \times 10^{-3}$ |
| 5g | 900° C. | 220° C. | $2.24 \times 10^{-3}$ |

Example 5

The general procedure of Example 3 is repeated with exceptions that the titanium dioxide DT51 is calcined at various temperatures (no calcination, 700, 800, or 900° C.) and that the impregnated support is also calcined at various temperatures (190° C. or 220° C.). The results are shown in Table 2, which indicate that the calcinations of the titanium dioxide prior to and after impregnation are both important to achieve high catalyst activity and stability.

Example 6

The catalyst prepared in Example 3 is used to prepare allyl acetate, which follows the same manner as the vinyl acetate preparation in Example 1 with the exception that the gas composition is 29% propylene, 60% helium, 7.7% oxygen and 3.3% acetic acid and the gas-hourly space velocity is 12,400 (ml/ml)/hr. The catalyst has an average rate of $4.48 \times 10^{-3}$ micromoles/s measured at the $6^{th}$ hour on stream.

Example 7

The general procedure of Example 4 is repeated with the exception that the ammonium persulfate concentration is varied from 0 to 0.1 molar in 0.025 molar increments. The results are shown in Table 3, which indicate that an optimum performance may exist at the ammonium persulfate concentrations between 0.05 and 0.075 molar.

TABLE 3

Effect of Ammonium Persulfate Concentration on Catalyst Activity Stability

| Ex. No. | Ammonium Persulfate Concentration, mol/l | Catalyst Activity at $1^{st}$ Hour (umol/s) | Catalyst Activity at $6^{th}$ Hour (umol/s) |
|---|---|---|---|
| 7a | No sulfate treatment | $3.02 \times 10^{-3}$ | $3.31 \times 10^{-3}$ |
| 7b | 0.025 | $3.70 \times 10^{-3}$ | $3.32 \times 10^{-3}$ |
| 7c | 0.050 | $3.94 \times 10^{-3}$ | $4.42 \times 10^{-3}$ |
| 7d | 0.075 | $4.94 \times 10^{-3}$ | $4.36 \times 10^{-3}$ |
| 7e | 0.10 | $3.10 \times 10^{-3}$ | $3.04 \times 10^{-3}$ |

I claim:

1. A method for preparing a supported palladium-gold catalyst, said method comprising
   (a) sulfating a titanium dioxide support with a sulfating agent selected from the group consisting of persulfuric acid, its salts, and mixtures thereof;
   (b) calcining the sulfated support;
   (c) impregnating the calcined support with a palladium salt, a gold salt, and an alkali metal or ammonium compound;
   (d) calcining the impregnated support; and
   (e) reducing the calcined support from step (d) to form the supported palladium-gold catalyst.

2. The method of claim 1, wherein the sulfating agent is ammonium persulfate.

3. The method of claim 1, wherein the calcining in step (b) is performed at a temperature within the range of 600° C. to 900° C.

4. The method of claim 3, wherein the temperature is within the range of 650° C. to 750° C.

5. The method of claim 1, wherein the alkali metal or ammonium compound is selected from the group consisting of hydroxides, carbonates, bicarbonates, metasilicates, and mixtures thereof.

6. The method of claim 1, wherein the alkali metal or ammonium compound is a carbonate or bicarbonate.

7. The method of claim 1, wherein the palladium and gold salts are selected from the group consisting of palladium chloride, sodium chloropalladite, palladium nitrate, palladium sulfate, auric chloride, tetrachloroauric acid, sodium tetrachloroaurate, and mixtures thereof.

8. The method of claim 1, wherein the calcination of step (d) is performed in a non-reducing atmosphere at a temperature within the range of 100° C. to 600° C.

9. The method of claim 8, the non-reducing atmosphere is selected from the group consisting of helium, nitrogen, argon, neon, nitrogen oxides, oxygen, air, carbon dioxide, and mixtures thereof.

10. The method of claim 8, wherein the calcination temperature is within the range of 100° C. to 300° C.

11. The method of claim 1, wherein the reduction is performed in hydrogen or a mixture of hydrogen and an inert gas.

12. The method of claim 11, wherein the reduction is performed at a temperature within the range of 300° C. to 600° C.

13. The method of claim 11, wherein the reduction is performed at a temperature within the temperature of 450° C. to 550° C.

14. The method of claim 1, which further comprises treating the supported palladium-gold catalyst from step (e) with a potassium salt.

15. A supported palladium-gold catalyst prepared by the method of claim 1.

16. A method for preparing vinyl acetate comprising oxidizing ethylene in the presence of acetic acid and the supported palladium-gold catalyst of claim 15.

* * * * *